United States Patent
Lihard et al.

(10) Patent No.: US 11,382,856 B2
(45) Date of Patent: *Jul. 12, 2022

(54) COMPACT POWDER FREE OF SURFACE-TREATED TALC, BASED ON MICA, A NON-VOLATILE, NON-PHENYL SILICONE OIL AND AN AMORPHOUS HYDROCARBON-BASED BLOCK COPOLYMER

(71) Applicant: L'OREAL, Paris (FR)

(72) Inventors: Anne Lihard, Aulnay sous Bois (FR); Anne Simonnet, Lassigny (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/493,886

(22) PCT Filed: Mar. 12, 2018

(86) PCT No.: PCT/EP2018/056118
§ 371 (c)(1),
(2) Date: Sep. 13, 2019

(87) PCT Pub. No.: WO2018/166991
PCT Pub. Date: Sep. 20, 2018

(65) Prior Publication Data
US 2020/0085722 A1    Mar. 19, 2020

(30) Foreign Application Priority Data
Mar. 17, 2017 (FR) ...................... 1752183

(51) Int. Cl.
| | | |
|---|---|---|
| *A61K 8/90* | (2006.01) | |
| *A61K 8/02* | (2006.01) | |
| *A61K 8/26* | (2006.01) | |
| *A61K 8/891* | (2006.01) | |
| *A61Q 1/10* | (2006.01) | |
| *A61Q 1/12* | (2006.01) | |

(52) U.S. Cl.
CPC ............... *A61K 8/90* (2013.01); *A61K 8/022* (2013.01); *A61K 8/26* (2013.01); *A61K 8/891* (2013.01); *A61Q 1/10* (2013.01); *A61Q 1/12* (2013.01); *A61K 2800/30* (2013.01)

(58) Field of Classification Search
CPC ... A61K 8/90; A61K 8/02; A61K 8/26; A61K 8/891; A61Q 1/10; A61Q 1/12
See application file for complete search history.

(56) References Cited

U.S. PATENT DOCUMENTS

2014/0093461 A1   4/2014   MacDermott et al.
2015/0320647 A1   11/2015   Shirai et al.

FOREIGN PATENT DOCUMENTS

| JP | 7-89825 A | 4/1995 |
|---|---|---|
| JP | 2016-504295 A | 2/2016 |
| WO | WO 2012/163984 A2 | 12/2012 |
| WO | WO 2014/087183 A1 | 6/2014 |

OTHER PUBLICATIONS

International Search Report dated May 24, 2018 in PCT/EP2018/056118 filed on Mar. 12, 2018.
Japanese Office Action dated Sep. 23, 2020 in Japanese Patent Application No. 2019-550136, 5 pages.

*Primary Examiner* — Shirley V Gembeh
(74) *Attorney, Agent, or Firm* — Oblon, McClelland, Maier & Neustadt, L.L.P.

(57) ABSTRACT

The present invention thus relates to a solid composition, especially for coating keratin materials, more particularly for making up and/or caring for keratin materials such as the skin, in compact powder form, especially comprising a physiologically acceptable medium and containing at least:—an oily phase in an amount of at least 20% by weight relative to the total weight of the composition; said oily phase comprising at least one non-volatile non-phenyl silicone oil; and—a pulverulent phase in an amount of at least 40% by weight relative to the total weight of the composition; said pulverulent phase comprising at least mica particles; and—at least one amorphous hydrocarbon-based block copolymer; said composition not containing any talc particles that have not been surface-treated and being able to be obtained via a process comprising the following steps: (i) the oily phase, the amorphous hydrocarbon-based block copolymer, the pulverulent phase and the volatile solvent(s) are mixed to form a slurry; and (ii) the slurry is formed in a container by compacting, in particular pressing and/or suction, to obtain the composition in powder form. The invention also relates to a process for coating keratin materials, more particularly for making up and/or caring for keratin materials such as the skin, characterized in that it comprises the application to the keratin materials of a composition as defined previously.

20 Claims, No Drawings

COMPACT POWDER FREE OF SURFACE-TREATED TALC, BASED ON MICA, A NON-VOLATILE, NON-PHENYL SILICONE OIL AND AN AMORPHOUS HYDROCARBON-BASED BLOCK COPOLYMER

The present invention relates to a solid composition in compact powder form, especially comprising a physiologically acceptable medium, in particular for coating keratin materials, more particularly for making up and/or caring for keratin materials, such as the skin, said compact powder being prepared via a wet process.

Skin care and/or makeup compositions are generally used to give the skin, such as the face, an attractive colour, but also to hide skin imperfections, such as redness, marks, wrinkles and fine lines.

The function of the abovementioned powders is mainly to give colour, a matt effect and even, for those more particularly intended for facial skin, to improve the staying power of a foundation or, if used alone, to give coverage (foundation powder, eyeshadow or face powder). These presentation forms are particularly appreciated by users with regard to their lightness, softness, tack-free aspect or non-greasy feel.

In general, these compositions combine a pulverulent phase that is generally predominant with a binder phase usually featured by a liquid fatty phase. The pulverulent phase is formed essentially of fillers combined with pigments, the amount of these pigments being modified to afford the desired makeup effect, generally a colour effect.

To obtain a composition in solid, compacted form, it is known from the prior art to use compacted makeup powders formed by a mixture of powders with a fatty binder, which are put in form, for example, by compression.

However, these compact powders in particular have the drawback of being fragile. Thus, when the percentage of pigments increases in the product, its manufacture and its compacting become complicated or even impossible to perform at an industrial level given the quality and productivity requirements. Furthermore, large amounts of pulverulent phase in the compact powder do not give satisfactory sensory properties when the powder is picked up from its packaging and/or when it is applied to the surface of the skin to be made up. It is furthermore difficult for a formulator to obtain good staying power of the product on the skin. To overcome these drawbacks, if the amount of fatty binder is increased, this composition will have a tendency to become waxy, i.e. to harden during use to the point that it cannot be picked up.

Among the qualities desired for compact makeup powders, mention may be made of:
good cohesion and homogenization of the composition,
good impact strength,
a good texture,
suitable hardness,
good adhesion to the skin,
good uptake irrespective of the applicator (in terms of sufficient amount of product),
comfort on application without a drying-out effect on the skin,
good staying-power properties of the powder,
good sensory properties at the time of pick-up,
good sensory properties at the time of application of the product.

It is known practice from the prior art, for the manufacture of such compositions, to use volatile organic solvents (isododecane or isopropanol) used in a wet preparation process known as a Wet Process, so as to inject one or more given foundation powders into a respective cup. These solvents allow fluidization of the powder and the formation of a "slurry" and forming thereof in a cup, and then evaporate off.

Compact powders obtained via this wet process technique have already been proposed in patent application EP 2928438; said powders comprising
an oily phase in an amount of at least 20% by weight relative to the total weight of the composition, and
at least one pulverulent phase in an amount of at least 40% by weight relative to the total weight of the composition, and
at least one hydrophobic film-forming polymer.

However, some of these formulations comprising untreated talc are not entirely satisfactory as regards the impact strength, the pick-up of the powder from its packaging and as regards the deposition of the product on the skin (pay-off), especially with certain applicators such as foam applicators and brushes.

There is thus still a need for novel care and/or makeup compact cosmetic powders which have a good texture, good cohesion and good impact strength and which are easy to pick up and to apply irrespective of the applicator, especially a brush do not have the drawbacks mentioned previously.

The Applicant has discovered, surprisingly, that this objective was achieved with a solid composition, especially for coating keratin materials, more particularly for making up and/or caring for keratin materials such as the skin, in compact powder form, especially comprising a physiologically acceptable medium and containing at least:
an oily phase in an amount of at least 20% by weight relative to the total weight of the composition; said oily phase comprising at least one non-volatile non-phenyl silicone oil; and
a pulverulent phase in an amount of at least 40% by weight relative to the total weight of the composition; said pulverulent phase comprising at least mica particles; and
at least one amorphous hydrocarbon-based block copolymer;
said composition not containing any talc particles that have not been surface-treated and being able to be obtained via a process comprising the following steps:
(i) the oily phase, the amorphous hydrocarbon-based block copolymer, the pulverulent phase and the volatile solvent(s) are mixed to form a slurry; and
(ii) the slurry is formed in a container by compacting, in particular pressing and/or suction, to obtain the composition in powder form.

The compact powder according to the invention has, irrespective of the tint, a pleasant creamy texture, good cohesion and homogenization, good sensory properties, good impact strength, and ease of pick-up and of application to keratin materials such as the skin, irrespective of the applicator and especially with a brush.

This discovery forms the basis of the invention.

The present invention thus relates to a solid composition, especially for coating keratin materials, more particularly for making up and/or caring for keratin materials such as the skin, in compact powder form, especially comprising a physiologically acceptable medium and containing at least:
an oily phase in an amount of at least 20% by weight relative to the total weight of the composition; said oily phase comprising at least one non-volatile non-phenyl silicone oil; and a pulverulent phase in an amount of at least 40% by weight relative to the total weight of the composition; said pulverulent phase comprising at least mica particles; and at least one amorphous hydrocarbon-based block copolymer;

said composition not containing any talc particles that have not been surface-treated and being able to be obtained via a process comprising the following steps:

(i) the oily phase, the amorphous hydrocarbon-based block copolymer, the pulverulent phase and the volatile solvent(s) are mixed to form a slurry; and (ii) the slurry is formed in a container by compacting, in particular pressing and/or suction, to obtain the composition in powder form.

The invention also relates to a process for coating keratin materials, more particularly for making up and/or caring for keratin materials such as the skin, characterized in that it comprises the application to the keratin materials of a composition as defined previously.

Definitions

In the context of the present invention, the term "keratin material" especially means the skin (of the body, face, around the eyes, or the eyelids).

The term "physiologically acceptable" means compatible with the skin and/or its integuments, which has a pleasant colour, odour and feel, and which does not cause any unacceptable discomfort (stinging or tautness) liable to discourage the consumer from using this composition.

The term "talc particle" refers to hydroxylated magnesium silicate particles of molecular formula $Mg_3Si_4O_{10}(OH)_2$ known as talc and belonging to the chemical family of phyllosilicates.

The term "talc particle that is not surface-treated" refers to any talc particle that is not surface-coated, for instance a surface treatment agent chosen from silicones, amino acids, fluoro derivatives or any other substance that promotes the dispersion and compatibility of the filler in the composition.

The term "composition not containing any talc particles that are not surface-treated" refers to any composition containing less than 1% by weight relative to the total weight of the composition, or even less than 0.5% by weight, or even less than 0.1% by weight, or even free of talc particles that are not surface treated.

For the purposes of the present invention, the following definitions apply:

"solid" means the state of the composition at room temperature (25° C.) and at atmospheric pressure (760 mmHg), i.e. a composition of high consistency, which conserves its form during storage. As opposed to "fluid" compositions, it does not flow under its own weight. It is advantageously characterized by a hardness as defined below.

"compact powder" means a mass of product whose cohesion is at least partly provided by compacting or, preferably, pressing during the manufacture. In particular, by taking a measurement using a TA.XT.plus Texture Analyser texturometer sold by the company Stable Micro Systems, the compact powder according to the invention may advantageously have a pressure resistance of between 0.1 and 1 kg and especially between 0.2 and 0.8 kg, relative to the surface area of the spindle used (in the present case 7.07 mm²). The measurement of this resistance is performed by moving an SMS P/3 flat-headed cylindrical spindle in contact with the powder over a distance of 2 mm and at a speed of 0.5 mm/second; more generally, this powder may be obtained by compacting or, preferably, by pressing.

Preferably, the composition according to the invention comprises less than 3% by weight and preferably less than 2% by weight of water relative to the total weight of the composition, or even is free of water.

The composition according to the invention advantageously comprises a solids content of greater than or equal to 95%, better still 98%, or even equal to 100%.

For the purposes of the present invention, the term "solids content" denotes the content of non-volatile matter.

The amount of solids content (abbreviated as SC) of a composition according to the invention is measured using a Halogen Moisture Analyzer HR 73 commercial halogen desiccator from Mettler Toledo. The measurement is performed on the basis of the weight loss of a sample dried by halogen heating, and thus represents the percentage of residual matter once the water and the volatile matter have evaporated off. This technique is fully described in the machine documentation supplied by Mettler Toledo.

The measurement protocol is as follows:

Approximately 2 g of the composition, referred to hereinbelow as the sample, are spread out on a metal crucible, which is placed in the halogen desiccator mentioned above. The sample is then subjected to a temperature of 105° C. until a constant weight is obtained. The wet mass of the sample, corresponding to its initial mass, and the dry mass of the sample, corresponding to its mass after halogen heating, are measured using a precision balance.

The experimental error associated with the measurement is of the order of plus or minus 2%.

The solids content is calculated in the following manner:

Solids content (expressed as weight percentage)=
100×(dry mass/wet mass).

Oily Phase

The composition of the invention comprises an oily phase. Said phase is liquid (in the absence of structuring agent) at room temperature (20-25° C.). It is organic and water-immiscible.

The oily phase (or fatty phase) of the compositions according to the invention comprises at least one non-volatile, non-phenyl silicone oil and optionally additional oils, and also ingredients that are soluble or miscible in oils. It may be constituted of a single oil or of a mixture of several oils.

The term "oil" refers to any fatty substance that is in liquid form at room temperature (20-25° C.) and at atmospheric pressure. These oils may be of plant, mineral or synthetic origin.

The additional oils may be chosen from the group constituted of hydrocarbon-based oils, silicone oils and fluoro oils, and mixtures thereof. They may be volatile or non-volatile.

The term "oil" refers to a fatty substance that is liquid at room temperature (25° C.) and atmospheric pressure (760 mmHg, i.e. $10^5$ Pa).

For the purposes of the present invention, the term "silicone oil" refers to an oil comprising at least one silicon atom, and especially at least one Si—O group, and more particularly an organopolysiloxane.

The term "fluoro oil" refers to an oil comprising at least one fluorine atom.

The term "hydrocarbon-based oil" refers to an oil mainly containing hydrogen and carbon atoms and possibly one or more functions chosen from hydroxyl, ester, ether and carboxylic functions.

For the purposes of the invention, the term "volatile oil" refers to any oil that is capable of evaporating on contact with the skin in less than one hour, at room temperature and atmospheric pressure. The volatile oil is a volatile cosmetic compound, which is liquid at room temperature, especially having a non-zero vapour pressure, at room temperature and atmospheric pressure, especially having a vapour pressure ranging from 0.13 Pa to 40 000 Pa ($10^{-3}$ to 300 mmHg), in particular ranging from 1.3 Pa to 13,000 Pa (0.01 to 100 mmHg) and more particularly ranging from 1.3 Pa to 1300 Pa (0.01 to 10 mmHg).

The term "non-volatile oil" refers to an oil that remains on the skin or the keratin fibre at room temperature and atmospheric pressure for at least several hours, and that especially has a vapour pressure of less than $10^{-3}$ mmHg (0.13 Pa).

The oily phase of the compositions according to the invention is present in a concentration of at least 20% by weight and preferably ranging from 25% to 50% by weight relative to the total weight of the composition.

Non-Volatile Non-Phenyl Silicone Oils

The oily phase of the composition according to the invention comprises at least one non-volatile non-phenyl silicone oil.

The term "non-phenyl silicone oil" refers to an oil comprising at least one silicon atom, and especially at least one Si—O group, and more particularly an organopolysiloxane but not containing a phenyl group.

The non-volatile non-phenyl silicone oils are preferably chosen from oils with a viscosity at 25° C. ranging from 8 to 5000 centistokes (cSt) ($10^{-6}$ m$^2$/s), more preferentially from 10 to 1000 cSt, more particularly from 50 to 500 cSt, and better still from 50 to 150 cSt. The viscosity may be measured according to standard DIN53018.

Among the non-phenyl silicone oils, use may be made more particularly of those corresponding to the following formula:

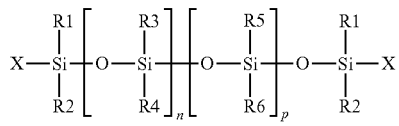

in which:

R1, R2, R5 and R6, which may be identical or different, denote an alkyl radical containing from 1 to 6 carbon atoms, R3 and R4, which may be identical or different, denote an alkyl radical containing from 1 to 6 carbon atoms, a vinyl radical, an amine radical or a hydroxyalkyl radical containing from 1 to 6 carbon atoms, X denotes an alkyl radical containing from 1 to 6 carbon atoms, an amine radical or a hydroxyalkyl radical containing from 1 to 6 carbon atoms, n and p are integers such that the compound is liquid.

As non-volatile non-phenyl silicone oils, use will be made more particularly of the polydimethylsiloxanes (INCI name: Dimethicone) (all the radicals R1 to R6 and X represent methyl), in particular with a viscosity from 50 to 500 cSt, especially 350 cSt, such as the commercial products sold under the names Belsil DM 350® from the company Wacker, and Xiameter PMX-200 Silicone Fluid® 350 CS from the company Dow Corning, and more particularly the polydimethylsiloxanes (INCI name: Dimethicone) with a viscosity from 50 to 150 cSt, especially 100 cSt, such as the commercial products sold under the names Belsil DM 100® from the company Wacker, and Xiameter PMX-200 Silicone Fluid 100 CS® from the company Dow Corning.

The non-volatile non-phenyl silicone oil(s)s are preferably present in a concentration ranging from 4% to 15% by weight and more preferentially from 5% to 10% by weight relative to the total weight of the composition.

Additional Non-Volatile Oils

The oily phase of the composition of the invention may also comprise at least one additional non-volatile oil.

As examples of additional non-volatile oils that may be used in the invention, mention may be made of:

hydrocarbon-based oils of plant origin, such as of fatty acid triglycerides containing from 4 to 24 carbon atoms, for instance caprylic/capric acid triglycerides, such as those sold by the company Stéarineries Dubois or those sold under the names Miglyol 810®, 812® and 818® by Dynamit Nobel; triglycerides of branched $C_{18}$-$C_{36}$ fatty acids and of glycerol, such as that sold under the name DUB TGI 24® by Stéarineries Dubois (INCI name C18-36 Acid Triglyceride);

linear or branched hydrocarbons, of mineral or synthetic origin, such as liquid paraffins and derivatives thereof, petroleum jelly, polydecenes, polybutenes, hydrogenated polyisobutene such as Parleam, or squalane;

synthetic ethers containing from 10 to 40 carbon atoms, such as dicaprylyl ether;

synthetic esters, especially of fatty acids, isononyl isononanoate, isopropyl myristate, isopropyl palmitate, C12 to C15 alkyl benzoate, hexyl laurate, diisopropyl adipate, 2-ethylhexyl palmitate, 2-octyldodecyl stearate, 2-octyldodecyl erucate, isostearyl isostearate, diisostearyl malate and tridecyl trimellitate;

fatty alcohols that are liquid at room temperature, containing a branched and/or unsaturated carbon chain containing from 12 to 26 carbon atoms, for instance octyldodecanol, isostearyl alcohol, 2-butyloctanol, 2-hexyldecanol, 2-undecylpentadecanol or oleyl alcohol;

higher fatty acids, such as oleic acid, linoleic acid or linolenic acid;

carbonates, such as dicaprylyl carbonate;

acetates;

citrates;

optionally partially hydrocarbon-based and/or silicone fluoro oils, for instance fluorosilicone oils, fluoropolyethers and fluorosilicones as described in EP-A-847 752;

silicone oils such as phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethyl-siloxysilicates; and mixtures thereof.

Volatile Oils

According to a particular form of the invention, the composition according to the invention may also comprise in the oily phase at least one volatile oil.

The volatile oils may be chosen from hydrocarbon-based volatile oils and silicone volatile oils, and mixtures thereof.

As examples of volatile hydrocarbon-based oils that may be used in the invention, mention may be made of volatile hydrocarbon-based oils chosen from hydrocarbon-based oils containing from 8 to 16 carbon atoms, and especially C8-C16 isoalkanes of petroleum origin (also known as isoparaffins), such as isododecane (also known as 2,2,4,4,6-pentamethylheptane), isodecane or isohexadecane, for example the oils sold under the Isopar or Permethyl trade names, branched $C_8$-$C_{16}$ esters, isohexyl neopentanoate, and mixtures thereof. Other volatile hydrocarbon-based oils, for instance petroleum distillates, especially those sold under the name Shell Solt by the company Shell, may also be used; volatile linear alkanes, such as those described in patent application DE10 2008 012 457 from the company Cognis.

Volatile silicone oils that may be mentioned include volatile linear or cyclic silicone oils, especially those with a viscosity ≤8 centistokes ($8×10^{-6}$ $m^2/s$) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Pulverulent Phase

The pulverulent phase comprises fillers and, preferentially, pigments.

A solid composition according to the invention advantageously has a content of pulverulent phase of greater than or equal to 35% by weight, in particular greater than or equal to 40% by weight, more particularly ranging from 50% to 80% by weight and better still from 60% to 75% by weight relative to the total weight of the composition.

According to a particular form of the invention, the amount of oily phase and the amount of pulverulent phase are such that the oily phase/pulverulent phase weight ratio ranges from 20/80 to 45/55, preferably from 25/75 to 40/60.

The term "fillers" should be understood as meaning colourless or white solid particles of any form, which are in a form that is insoluble and dispersed in the medium of the composition. Mineral or organic in nature, they make it possible to confer softness to the composition, a matt effect and uniformity to the makeup.

Micas

The pulverulent phase according to the invention comprises at least mica particles.

Mica is the name of a family of minerals, of the group of silicates, subgroup of phyllosilicates, formed mainly from potassium aluminium silicate. It is characterized by its laminated structure (phyllosilicates).

It is characterized by its laminated structure (phyllosilicates) usually in the form of flakes, its metallic glint and its high heat resistance. The properties of micas, their transparency, their heterogeneity, their thermal properties and their good electrical insulation are such that they are found in many uses.

The micas used according to the present invention preferably have a mean size of less than or equal to 100 µm, more preferentially from 1 to 60 µm and even more preferentially from 1 to 20 µm.

The term "mean particle size" means the median volume size D[50] representing the maximum size of 50% by volume of the particles. The sizes are measured by static light scattering using a commercial MasterSizer 3000 particle size analyser from Malvern, which makes it possible to determine the particle size distribution of all of the particles over a wide range which may extend from 0.01 µm to 1000 µm. The data are processed on the basis of the standard Mie scattering theory. This theory is the most suitable for size distributions ranging from submicron to multimicron; it allows an "effective" particle diameter to be determined. This theory is especially described in the publication by Van de Hulst, H. C., *Light Scattering by Small Particles*, Chapters 9 and 10, Wiley, New York, 1957. D[50] represents the maximum size of 50% by volume of the particles.

The mica used in the composition according to the invention is in pure form. Use will preferably be made of:
  sericites such as the commercial product Sericite S-152-BC® (mean size 6 µm) from the company Miyoshi Kasei;
  muscovite micas (CI77019) (INCI name: mica) such as the commercial product Mearlmica DD® and Mearlmica SV® from BASF, Sumicos Velvet Mica 43037® from Sudarshan Chemical;
  synthetic fluorophlogopite micas (INCI name: Synthetic Fluorophlogopite) such as the commercial product Synafil S115® (mean size 7.6 µm) from the company Eckart;
  mixtures thereof.

Use will be made more preferentially of synthetic fluorophlogopite mica particles (INCI name: Synthetic Fluorophlogopite) such as the commercial product Synafil S115® (mean size 7.6 µm) from the company Eckart.

The mica particles are preferably present in the pulverulent phase in amounts ranging from 1% to 70% by weight and more preferentially from 10% to 50% by weight relative to the total weight of the pulverulent phase.

Additional Fillers

The term "fillers" should be understood as meaning colourless or white solid particles of any form, which are in a form that is insoluble and dispersed in the medium of the composition. Mineral or organic in nature, they make it possible to confer softness to the composition, a matt effect and uniformity to the makeup.

The additional fillers used in the compositions according to the present invention may be of lamellar, globular, spherical or fibre form, or in any other form intermediate between these defined forms.

The additional fillers according to the invention may or may not be surface-coated, and in particular they may be surface-treated with silicones, amino acids, fluorinated derivatives or any other substance which promotes the dispersion and the compatibility of the filler in the composition.

Among the additional mineral fillers that may be used in the compositions according to the invention, mention may be made of surface-treated talcs, silica, magnesium aluminium silicate, trimethyl siloxysilicate, kaolin, bentone, calcium carbonate, magnesium hydrogen carbonate, hydroxyapatite, boron nitride, hollow silica microspheres (Silica Beads from Maprecos), glass or ceramic microcapsules, silica-based fillers, for instance Aerosil 200® or Aerosil 300®; Sunsphere H-33® and Sunsphere H-51® sold by Asahi Glass; Chemicelen sold by Asahi Chemical; composites of silica and of titanium dioxide, for instance the TSG series sold by Nippon Sheet Glass, and perlite powders, and mixtures thereof.

Among the additional organic fillers that may be used in the compositions according to the invention, mention may be made of polyamide powders (Nylon® Orgasol from Atochem), poly-β-alanine powders and polyethylene powders, polytetrafluoroethylene powders (Teflon®), lauroyllysine, starch, tetrafluoroethylene polymer powders, hollow polymer microspheres, for example comprising an (alkyl) acrylate, such as Expancel® (Nobel Industrie), metal soaps derived from organic carboxylic acids containing from 8 to 22 carbon atoms and preferably from 12 to 18 carbon atoms, for example zinc stearate, magnesium stearate, lithium stearate, zinc laurate, magnesium myristate, Polypore® L200 (Chemdal Corporation), silicone resin microbeads (for example Tospearl® from Toshiba), polyurethane powders, in particular powders of crosslinked polyurethane comprising a copolymer, said copolymer comprising trimethylol hexyl lactone, for instance the hexamethylene diisocyanate/trimethylol hexyl lactone polymer sold under the name Plastic Powder D-400® or Plastic Powder D-800® by the company Toshiki, carnauba microwaxes, such as the product sold under the name Micro Care 350® by the company Micro Powders, synthetic microwaxes, such as the product sold under the name MicroEase 114S® by the company Micro Powders, microwaxes formed from a mixture of carnauba wax and polyethylene wax, such as those sold under the names Micro Care 300® and 310® by the company Micro Powders, microwaxes formed from a mixture of carnauba wax and of synthetic wax, such as the product sold under the name Micro Care 325® by the company Micro Powders, polyethylene microwaxes, such as those sold under the names Micropoly 200®, 220®, 220L® and 250S® by the company Micro Powders; fibres of synthetic or natural, mineral or organic origin. They may be short or long, individual or organized, for example braided, hollow or solid. They may have any shape and may especially have a circular or polygonal (square, hexagonal or octagonal) cross section depending on the specific application envisaged. In particular, their ends are blunted and/or polished to prevent injury. The fibres have a length ranging from 1 µm to 10 mm, preferably from 0.1 mm to 5 mm and better still from 0.3 mm to 3 mm. Their cross section may be included in a circle with a diameter ranging from 2 nm to 500 µm, preferably ranging from 100 nm to 100 µm and better still from 1 µm to 50 µm. As fibres that may be used in the compositions according to the invention, mention may be made of non-rigid fibres such as polyamide (Nylon®) fibres or rigid fibres such as polyimideamide fibres, for instance those sold under the names Kermel® and Kermel Tech® by the company Rhodia or poly(p-phenyleneterephthalamide) (or aramid) fibres sold especially under the name Kevlar® by the company DuPont de Nemours, and mixtures thereof.

Particulate Colouring Agents

The particulate colouring agent or dyestuff according to the invention is preferably chosen from pigments, nacres and reflective particles, and mixtures thereof.

Pigments

The term "pigments" should be understood as meaning white or coloured, mineral or organic particles of any shape, which are insoluble in the physiological medium, and which are intended to colour the composition.

The pigments may be white or coloured, and mineral and/or organic.

Among the mineral pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminium powder and copper powder.

The organic pigments may be chosen from the materials below, and mixtures thereof:
 cochineal carmine,
 organic pigments of azo dyes, anthraquinone dyes, indigoid dyes, xanthene dyes, pyrene dyes, quinoline dyes, triphenylmethane dyes or fluoran dyes.

Among the organic pigments, mention may be made in particular of the D&C certified pigments known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The chemical materials corresponding to each of the organic dyestuffs mentioned previously are mentioned in the publication "International Cosmetic Ingredient Dictionary and Handbook", 1997 edition, pages 371 to 386 and 524 to 528, published by The Cosmetic, Toiletries and Fragrance Association, the content of which is incorporated into the present patent application by reference.

A composition according to the invention may comprise a content of pigments ranging from 0% to 30% by weight relative to the total weight of the composition, preferably ranging from 2% to 20% by weight and preferentially ranging from 4% to 10% by weight, relative to the total weight of the composition.

Nacres

The term "nacres" should be understood as meaning coloured particles of any form, which may or may not be iridescent, especially produced by certain molluscs in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, and nacreous pigments based on bismuth oxychloride. They may also be mica particles, at the surface of which are superposed at least two successive layers of metal oxides and/or of organic dyestuffs.

The nacres may more particularly have a yellow, pink, red, bronze, orangey, brown, green, blue, violet and/or coppery colour or glint.

As illustrations of nacres that may be introduced into the composition, mention may be made of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper glint sold especially by the company Engelhard under the name Copper 340A (Timica); the nacres with a red glint sold especially by the company Merck under the name Sienna fine (17386) (Colorona); the nacres with a yellow glint sold especially by the company Engelhard under the name Yellow (4502) (Chromalite); the red nacres with a gold glint sold especially by the company Engelhard under the name Sunstone G012 (Gemtone); the pink nacres sold especially by the company Engelhard under the name Tan opale G005 (Gemtone); the black nacres with a gold glint sold especially by the company Engelhard under the name Nu antique bronze 240 AB (Timica), the blue nacres sold especially by the company Merck under the name Matte blue (17433) (Microna), the white nacres with a silvery glint sold especially by the company Merck under the name Xirona Silver, and the golden-green pink-orange nacres sold especially by the company Merck under the name Indian summer (Xirona), and mixtures thereof.

Still as examples of nacres, mention may also be made of particles comprising a borosilicate substrate coated with titanium oxide.

Particles comprising a glass substrate coated with titanium oxide are sold in particular under the name Metashine MC1080RY by the company Toyal.

Finally, examples of nacres that may also be mentioned include polyethylene terephthalate flakes, especially those sold by the company Meadowbrook Inventions under the name Silver 1P 0.004×0.004 (silver flakes).

Reflective Particles

The term "reflective particles" denotes particles of which the size, the structure, in particular the thickness of the layer(s) of which they are made and their physical and chemical nature, and surface state, allow them to reflect incident light. This reflection may, if appropriate, have an intensity sufficient to create, at the surface of the composition or mixture, when the latter is applied to the substrate to be made up, highlight points visible to the naked eye, that is to say more luminous points which contrast with their surroundings by appearing to sparkle.

The reflective particles may be selected so as not to significantly alter the colouration effect generated by the colouring agents with which they are combined, and more particularly so as to optimize this effect in terms of colour yield. They may more particularly have a yellow, pink, red, bronze, orange, brown, gold and/or coppery colour or tint.

These particles may have varied forms and may especially be in platelet or globular form, in particular in spherical form.

Irrespective of their form, the reflective particles may or may not have a multilayer structure, and, in the case of a multilayer structure, may have, for example, at least one layer of uniform thickness, especially of a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be made of one or more organic and/or mineral materials.

More particularly, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material.

Reflective particles are described especially in JP-A-09188830, JP-A-10158450, JP-A-10158541, JP-A-07258460 and JP-A-05017710.

Mention may also be made, still by way of example of reflective particles comprising a mineral substrate coated with a layer of metal, of the particles comprising a borosilicate substrate coated with silver.

Particles with a silver-coated glass substrate, in the form of platelets, are sold under the name Microglass Metashine REFSX 2025 PS® by the company Toyal. Particles having a glass substrate coated with nickel/chromium/molybdenum alloy are sold under the name Crystal Star GF 550® and GF 2525® by this same company.

Use may also be made of particles comprising a metallic substrate such as silver, aluminium, iron, chromium, nickel, molybdenum, gold, copper, zinc, tin, manganese, steel, bronze or titanium, said substrate being coated with at least one layer of at least one metal oxide such as titanium oxide, aluminium oxide, iron oxide, cerium oxide, chromium oxide or silicon oxides, and mixtures thereof.

Examples that may be mentioned include aluminium powder, bronze powder or copper powder coated with $SiO_2$ sold under the name Visionaire by the company Eckart.

Preferably, the pulverulent phase comprises at least one compound chosen from:

organic pigments, for instance the pigments certified D&C by the Food & Drug Administration as listed in the section "Color Additives—Batch Certified by the U.S. Food and Drug Administration" of the CTFA; mention may be made especially of Blue 1 and 4, Brown 1, Ext. Violet 2, Ext. Yellow 7, Green 3, 5, 6 and 8, Orange 4, 5, 10 and 11, Red 4, 6, 7, 17, 21, 22, 27, 28, 30, 36 and 40, Violet 2, Yellow 5, 6, 7, 8, 10 and 11;

mineral pigments such as iron oxide, titanium oxide, zirconium oxide, cerium oxide, zinc oxide, iron oxide or chromium oxide, ferric blue, manganese violet, ultramarine blue, pink or violet, chromium hydrate, chromium hydroxide and bismuth oxychloride;

pearls, for instance mica coated with titanium oxide, mica coated with titanium oxide and iron oxide, and mica coated with an amino acid such as lauroyl lysine;

polyethylene terephthalate flakes;

sericite;

reflective particles, for instance particles comprising a borosilicate substrate coated with a metal layer;

mixtures thereof.

Amorphous Hydrocarbon-Based Block Copolymer

The composition according to the invention comprises at least one amorphous hydrocarbon-based block copolymer, preferably a block copolymer that is soluble or dispersible in the oily phase.

Such a copolymer may thus serve as gelling agent for this oily phase.

The hydrocarbon-based block copolymer may especially be a diblock, triblock, multiblock, radial or star copolymer, or mixtures thereof.

Such hydrocarbon-based block copolymers are described in patent application US-A-2002/005 562 and in patent U.S. Pat. No. 5,221,534.

The copolymer may contain at least one block whose glass transition temperature is preferably less than 20° C., preferably less than or equal to 0° C., preferably less than or equal to −20° C. and more preferably less than or equal to −40° C. The glass transition temperature of said block may be between −150° C. and 20° C. and especially between 100° C. and 0° C.

The hydrocarbon-based block copolymer present in the composition according to the invention is preferably an amorphous copolymer formed by polymerization of an olefin. The olefin may especially be an ethylenically unsaturated monomer.

Examples of olefins that may be mentioned include ethylenic carbide monomers, especially containing one or two ethylenic unsaturations and containing from 2 to 5 carbon atoms, such as ethylene, propylene, butadiene, isoprene or pentadiene.

Advantageously, the hydrocarbon-based block copolymer is an amorphous block copolymer of styrene and of an olefin.

Block copolymers comprising at least one styrene block and at least one block comprising units chosen from butadiene, ethylene, propylene, butylene and isoprene or a mixture thereof are especially preferred.

According to a preferred embodiment, the hydrocarbon-based block copolymer is hydrogenated to reduce the residual ethylenic unsaturations after the polymerization of the monomers.

In particular, the hydrocarbon-based block copolymer is a copolymer, optionally hydrogenated, containing styrene blocks and ethylene/C3-C4 alkylene blocks.

Diblock copolymers, which are preferably hydrogenated, that may be mentioned include styrene-ethylene/propylene copolymers, styrene-ethylene/butadiene copolymers and styrene-ethylene/butylene copolymers. Diblock polymers are especially sold under the name Kraton® G1701E by the company Kraton Polymers.

Triblock copolymers, which are preferably hydrogenated, that may be mentioned include styrene-ethylene/propylene-styrene copolymers, styrene-ethylene/butadiene-styrene copolymers, styrene-ethylene/butylene-styrene copolymers, styrene-isoprene-styrene copolymers and styrene-butadiene-styrene copolymers. Triblock polymers are especially sold under the names Kraton® G1650, Kraton® G1652, Kraton® D1101, Kraton® D1102 and Kraton® D1160 by the company Kraton Polymers.

According to one embodiment of the present invention, the hydrocarbon-based block copolymer is a styrene-ethylene/butylene-styrene triblock copolymer.

According to a preferred embodiment of the invention, it is especially possible to use a mixture of a styrene-butylene/ethylene-styrene triblock copolymer and of a styrene-ethylene/butylene diblock copolymer, especially the products sold under the name Kraton® G1657M by the company Kraton Polymers.

Preferably, a composition according to the invention comprises a content of from 0.5% to 5% by weight and better still from 0.5% to 2% by weight of active material of hydrocarbon-based block copolymer(s) relative to the total weight of the composition.

Preferably, the amorphous hydrocarbon-based block copolymer and the non-volatile hydrocarbon-based oil chosen from $C_{12}$-$C_{15}$ alkyl benzoate(s) are present in the composition in a respective total content such that the weight ratio of the amorphous hydrocarbon-based block copolymer to said $C_{12}$-$C_{15}$ alkyl benzoate(s) is inclusively between 0.06 and 0.3 and better still between 0.08 and 0.2.

Aqueous Phase

The composition according to the invention may comprise an aqueous phase comprising water and optionally other water-soluble or water-miscible ingredients.

This aqueous phase, when present, is used in an amount that is compatible with the pulverulent presentation form required according to the invention.

The aqueous phase may be a demineralized water or alternatively a floral water such as cornflower water and/or a mineral water such as Vittel water, Lucas water or La Roche Posay water and/or a spring water.

The aqueous phase may also comprise a polyol that is miscible with water at room temperature (25° C.) chosen especially from polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol (C1-C4)alkyl ethers, mono-, di- or triethylene glycol (C1-C4)alkyl ethers; and mixtures thereof.

The composition according to the invention may comprise a polyol that is miscible with water at room temperature. Such polyols may promote the moisturization of the surface of the skin on which the composition is applied.

In addition, the composition according to the invention may comprise a monoalcohol containing from 2 to 6 carbon atoms, such as ethanol or isopropanol.

A composition according to the invention advantageously comprises less than 5% by weight of aqueous phase, and in particular of water, relative to the total weight of the composition. Preferentially, a composition according to the invention is free of aqueous phase, and in particular free of water.

Adjuvants

The composition may comprise other ingredients (adjuvants) usually used in cosmetics, such as preserving agents, cosmetic active agents, moisturizers, UV-screening agents, thickeners and fragrances.

Needless to say, a person skilled in the art will take care to select the optional adjuvant(s) added to the composition according to the invention such that the advantageous properties intrinsically associated with the composition in accordance with the invention are not, or are not substantially, adversely affected by the envisioned addition.

Preparation Process (Wet Process)

The cosmetic composition according to the invention is obtained via a wet process comprising the following steps:
    the oily phase, the amorphous hydrocarbon-based block copolymer, the pulverulent phase and at least one volatile solvent are mixed to form a slurry;
    said slurry is formed in a container by compacting, in particular pressing and/or suction, to obtain the final compact powder.

Preferentially, a step of drying the slurry moulded in the container is also performed.

Mixing Step

In this step, the components of the oily phase, the components of the pulverulent phase and the volatile solvent(s) are mixed to prepare the slurry, which is a thick suspension of the pulverulent materials in the liquid formed by the oily phase and the volatile solvent.

According to a first variant, the components of the pulverulent phase and those of the oily phase are premixed and, in a second stage, the volatile solvent(s) are then added to the mixture obtained.

According to a second variant, the components of the oily phase and the volatile solvent(s) are premixed and, in a second stage, the components of the pulverulent phase are then added to the mixture obtained.

According to a particular form of the invention, the amount of oily phase and the amount of pulverulent phase are such that the oily phase/pulverulent phase weight ratio ranges from 20/80 to 45/55, preferably from 25/75 to 40/60.

The volatile solvents may be chosen from water, $C_1$-$C_4$ monoalcohols such as ethanol or isopropanol, ethers such as dicaprylyl ether, fluorocarbon solvents, cyclic or linear silicone volatile silicone oils and hydrocarbons, for instance isoparaffins such as isododecane. Preferentially, use will be made of $C_1$-$C_4$ monoalcohols, such as ethanol or isopropanol, and isoparaffins such as isododecane, and mixtures thereof.

According to the present invention, the mixing with the pulverulent phase may be performed with any type of mixer such as a Lodige mixer.

According to a particular form of the invention, the mixed powder may also undergo milling, for example with an Alpine pin mill.

According to a particular form of the invention, the mixing of the volatile solvents may be performed in any suitable container such as a bowl. It may be performed in a planetary mixer. The dispersion time required is not limited and may depend on certain factors such as the type of mixer. For example, if a planetary mixer is used, the dispersion time may range from 15 to 20 minutes.

The total amount of oily phase, of pulverulent phase and of volatile solvent is not limited. According to a particular form of the invention, the weight ratio of the total amount of oily phase and pulverulent phase/amount of volatile solvent (s) may be 5/1, preferably 3/1 and more preferentially 2/1.

If necessary, degassing may be performed during the mixing step. The oily phase, the pulverulent phase and the volatile solvent(s) may be mixed in a vacuum chamber. The degassing time may depend on certain factors such as the pressure in the vacuum chamber. It may range from 15 to 20 minutes. It is preferable to stir the slurry for efficient degassing.

Forming Step

In this step, the slurry is formed in a container by compacting, in particular pressing and/or suction.

A crucible or a cuvette may be used as container. The container may have small orifices which allow only the solvent to escape by suction.

As methods for pouring the slurry into the container, mention may be made of those by injection via the top of the container (top injection) or by injection via the rear of the container (back injection).

In the "top injection" method, the slurry is poured into the container from above the container. This method is particularly suitable for preparing multi-coloured compact powders.

In the "back injection" method, the slurry is injected via the base of the container by means of a suitable mechanism for introducing it into the container. This injection method is suitable for a wide range of compact makeup powders and is particularly suitable for obtaining a compact powder of complex form. The slurry introduced into the container is moulded by compression and/or suction. Preferably, the compression and suction are performed simultaneously.

Compacting, in particular pressing, may be performed by exerting pressure on the slurry in the container via mechanical means such as a press having a surface that may or may not be flat (possibility of relief). Suction may be performed, for example, by reducing the pressure in the container by vacuum. The compacting, in particular pressing, and suction may be repeated several times. If necessary, vibration may be supplied to the container and/or the press.

Drying Step

In this step, the moulded slurry is dried to obtain a compact powder free of volatile solvent or containing a very small amount of volatile solvent. By drying, the remaining volatile solvent(s) may be totally removed. The drying temperature and time depend on several factors such as the components of the composition and the type of volatile solvent used. For example, drying may be performed at a temperature of from 60 to 100° C. for a time of 1 to 12 hours.

Cosmetic Process

The invention also relates to a process for coating keratin materials, more particularly for making up and/or caring for keratin materials such as the skin, in particular the face or the eyelids, characterized in that it comprises the application to said keratin materials of a composition as defined previously.

Preferentially, the cosmetic composition according to the invention may be a foundation powder, a face powder or an eyeshadow.

The cosmetic composition according to the invention may be applied by means of any applicator suitable for compact powders intended to be applied to the face or to the eyelids, such as a powder puff or a brush.

Such compositions are especially prepared according to the general knowledge of a person skilled in the art.

Assembly

According to another aspect, the invention also relates to a cosmetic assembly comprising:
i) a container delimiting one or more compartment(s), said container being closed by a closing member and optionally not being leaktight; and
ii) a makeup and/or care composition in accordance with the invention placed inside said compartment(s).

The container may be, for example, in the form of a jar or a box. The closing member may be in the form of a lid comprising a cap mounted so as to be able to move by translation or by pivoting relative to the container housing said makeup and/or care composition(s).

Said cosmetic assembly may be combined with an applicator such as a powder puff, a foam applicator or a brush.

Throughout the description, including the claims, the term "comprising a" should be understood as being synonymous with "comprising at least one", unless otherwise specified.

The expressions "between . . . and . . . ", and "ranging from . . . to . . . " should be understood as meaning limits included, unless otherwise specified. The invention is illustrated in greater detail by the examples and figures presented below. Unless otherwise indicated, the amounts shown are expressed as weight percentages.

EXAMPLE 1: NACREOUS TINTED POWDERED EYESHADOW

| Phase | Ingredients | Amounts in weight % |
|---|---|---|
| P1 | Boron nitride (Softouch Boron Nitride Powder CC6058 ® - Momentive Performance Materials) | 3 |
| | Magnesium stearate | 2 |
| | Synthetic fluorophlogopite (Synafil S115 ® - Eckart) | 3.4 |
| | Mica (Sericite S-152-BC ® - Miyoshi Kasei) | 2.1 |
| | Nylon-12 (Orgasol 2002 EXD NAT COS - Arkema) | 4 |
| | Talc (and) methicone (SI-2 Talc JA-46R - Daito Kasei Kogyo) | 5 |
| | Black iron oxides CI 77499 (Sunpuro Black Iron Oxide C33-7001 ® - Sun) | 4.9 |
| P2 | Calcium aluminium borosilicate (and) silver (Metashine MT1030PS ® - Nippon Sheet Glass) | 40 |
| | Iron oxide (and) mica (and) titanium dioxide (Colorona Mica Black ® - Merck) | 10 |
| L1 | Phenyl trimethicone (Dow Corning 556 Cosmetic Grade Fluid) | 6 |
| | C12-15 Alkyl benzoate (Finsolv TN ® - Innospec Active Chemicals) | 12.8 |
| | Hydrogenated styrene/butadiene copolymer | 1.2 |

-continued

| Phase | Ingredients | Amounts in weight % |
|---|---|---|
| L2 | (Kraton G1657 MS SQR 1111 ® - Kraton Polymers)<br>Dimethicone 100 cSt<br>(Belsil DM 100 ® - Wacker)<br>Caprylyl glycol<br>Sorbitan isostearate | 5<br>0.5<br>0.1 |

Preparation Process:

The procedure below was used to prepare the compositions according to the invention.

1—Preparation of the Pulverulent Phase P1/P2:

The compounds of phase P1 and the pigments of phase P1 are weighed out in a large stainless-steel crucible and then milled using a shredder, first once for 15 seconds at 1500 rpm and then three times for 1 minute at 3000 rpm.

The nacres of phase P2 are weighed out in a second crucible and added to phase P1, and the preparation (phase P1+phase P2) is then milled in a shredder (R5 or R5 plus) twice for 15 seconds at 1500 rpm.

2—Preparation of Phase L1:

The compounds $C_{12}$-15 alkyl benzoate and phenyl trimethicone are weighed out in a beaker and then heated to 100° C. The polymer is then added and the mixture is stirred using a deflocculator (Turbotest 33/300 PH—Rayneri, VMI Group) until a vortex forms (about 300 rpm) until a homogeneous liquid is obtained.

3—Incorporation of the Binder Phase (L1/L2):

The compounds of phase L2 and phase L1 are weighed out in a small stainless-steel crucible. The assembly is heated to 45° C. on a hotplate and then added to the pulverulent phase in a kneader (Kenwood KMY90 Major Titanium kneader). The mixture is kneaded first once for 1 minute at the minimum speed and then once for 30 seconds still at the minimum speed of the machine.

4—Finishing of the Preparation:

The powder obtained is then diluted in isododecane. The amount of water is between 20% and 40% by weight relative to the total weight of the composition so as to obtain a viscosity suitable for a Pilote Back Injection machine sold by the company Plàsticos T3, S.A. This Back Injection machine makes it possible to inject the "powder-isododecane" mixture, also known as a slurry, via the base of the cup and simultaneously to draw off part of the dilution isododecane by suction. Throughout the injection of the product, the injection mould is placed under vacuum so as to allow the removal of the isododecane, which is drawn off by suction and recovered in the vacuum trap. Placing under vacuum thus promotes the filling and homogenization of the cup.

The parts back-injected are then placed in a ventilated oven at 45° C. until their weight no longer changes. The product is then considered as being dry.

Measurement of the Impact Strength:

Measurement Principle

The machine used to perform such a measurement, known as a Package Drop-Test machine sold by the company Co Pack (Italy), makes it possible to perform drop tests on the solid compositions in compact powder form to measure their impact strength. The drop height is 30 cm. By means of a small ruler, the size of the support that holds the compact is set (according to the size of the crucible) and the compact is then dropped by means of compressed air that actuates the aperture of the support. The number of drops required to split the powder is measured.

The test is performed on five dishes. The drop test is considered satisfactory when the mean of the number of drops is greater than or equal to 10.

The pick up and pay off of Example 1 were measured with a foam applicator and a brush, as was the impact strength.

Measurement of the Pick Up/Pay Off with a Foam Applicator

> Equipment

Caressa foam applicator (ref. 1001486—Kahn)

Supplale Support (manufacturer: Idemistupetrochemical; composition: collagen sheet with artificial relief bonded on a fabric)

powder sample already used at least once and not visually damaged

Hotplate (ref. PCMF 400×600—Ekium)

Measurement Principle

A piece of supplale is placed on the hotplate so as to temper it at 32° C. The product is picked up by performing three times a transverse movement holding the applicator parallel to the surface of the powder and perpendicular to the direction of movement.

The product is then deposited on the supplale by performing three times a transverse movement, holding the applicator parallel to the surface of the supplale and perpendicular to the direction of movement. The application area is about 3.5 cm long and the width of the applicator.

The result obtained is then graded on a scale from 0 to 5 according to the intensity relative to preestablished boundaries.

5 equivalent to very good 4 equivalent to good 3 equivalent to moderate 2 equivalent to mediocre 1 equivalent to poor 0 equivalent to impossible A difference of 1 is considered as significant.

Measurement of the Pick Up/Pay Off with a Brush

> Equipment

Eyeshadow Brush M applicator brush—Suqqu

Supplale Support (manufacturer: Idemistupetrochemical; composition: collagen sheet with artificial relief bonded on a fabric) preheated on a hotplate to 32° C.

dish already used at least once and not visually damaged

Measurement Principle

A piece of supplale is placed on the hot plate so as to temper it at 32° C.

The product is picked up by performing three times a transverse movement, holding the brush at an angle of about 45° relative to the surface of the powder and parallel to the direction of movement.

The product is then deposited on the supplale by performing three times a transverse movement, holding the brush at an angle of about 45° relative to the surface of the supplale and parallel to the direction of movement. The application area is about 3.5 cm long and the width of the brush.

The result obtained is then graded on a scale from 0 to 5 according to the intensity relative to preestablished boundaries.

5 equivalent to very good 4 equivalent to good 3 equivalent to moderate 2 equivalent to mediocre 1 equivalent to poor 0 equivalent to impossible.

A difference of 1 is considered as significant.

The results of the comparative tests are given in the table below:

| Evaluations | Ex. 1 |
|---|---|
| Pick up/pay off with a foam applicator | 5 |
| Pick up/pay off with a brush | 5 |
| Impact strength | 15 |

The compact powder of Example 1 showed excellent pick up/pay off qualities both with the applicator foam and with a brush, and also good impact strength.

EXAMPLES 2 TO 5: NACREOUS TINTED POWDERED EYESHADOWS (REVELATION OF SILICONE OIL IN THE BINDER PHASE)

The following compositions were prepared according to the same preparation method indicated for Example 1, except that the pulverulent phase comprises only phase P1 and does not comprise the nacre-based phase P2.

| Phase | Ingredients | Ex. 2 | Ex. 3 | Ex. 4* | Ex. 5* |
|---|---|---|---|---|---|
| P1 | Synthetic fluorophlogopite (Synafil S115 ® - Eckart) | 13.9 | 13.9 | 13.9 | 13.9 |
| | Mica (Mearlmica SV) | 10 | 10 | 10 | 10 |
| | Mica (Sericite S-152-BC ®- Miyoshi Kasei) | 12 | 12 | 12 | 12 |
| | Boron nitride (Softouch Boron Nitride Powder CC6058 ® - Momentive Performance Materials) | 3 | 3 | 3 | 3 |
| | Nylon-12 (Orgasol 2002 EXD NAT COS ® - Arkema) | 4 | 4 | 4 | 4 |
| | Talc (and) methicone (surface-treated talc) (SI-2 Talc JA-46R ® - Daito Kasei Kogyo) | 5 | 5 | 5 | 5 |
| | Magnesium stearate | 2 | 2 | 2 | 2 |
| | Pigments: Titanium dioxide (Hombitan FF Pharma - Sachtleben) Iron oxide (Unipure Red LC 383 - Sensient) Iron oxides Sunpuro Red Iron Oxide C33-8001, Sunpuro Yellow Iron Oxide C33-9001, Sunpuro Black Iron Oxide C33-7001 - Sun) | 28 | 28 | 28 | 28 |
| L1 | Styrene/isoprene block copolymer (Kraton G1701 EU ®) | 0.72 | 0.72 | 0.72 | 0.72 |
| | Phenyl trimethicone (Dow Corning 556 ® Cosmetic Grade Fluid) | 3.6 | 3.6 | 3.6 | 3.6 |
| | C12-15 Alkyl benzoate (Finsolv TN ® - Innospec Active Chemicals) | 7.68 | 7.68 | 7.68 | 7.68 |
| L2 | Dimethicone 100 CST (Xiameter PMX-200 Silicone Fluid 100 CST) | 10 | — | — | — |
| | Phenyl trimethicone (phenyl silicone oil) Dow Corning 556 Cosmetic Grade Fluid ®) | — | — | 10 | — |
| | Dimethicone 350 CST (Xiameter PMX-200 ® Silicone Fluid 350 CST) | — | 10 | — | — |
| | Cyclopentasiloxane (Xiameter PMX-0245 ® Cyclopentasiloxane) | — | — | — | 10 |
| | Caprylyl glycol | 0.5 | 0.5 | 0.5 | 0.5 |
| | Sorbitan isostearate | 0.1 | 0.1 | 0.1 | 0.1 |

*outside the invention

For each of the Examples 2 to 5, the pick up/pay off with a foam applicator, the pick up/pay off with a brush and the impact strength were evaluated according to the same test protocols indicated for Example 1.

The results of the comparative tests are given in the table below:

| Evaluations | Ex. 2 | Ex. 3 | Ex. 4* | Ex. 5* |
|---|---|---|---|---|
| Pick up/pay off with a foam applicator | 5 | 3 | 1 | 2 |
| Pick up/pay off with a brush | 4 | 3 | 1 | 1 |
| Impact strength | 13 | 12.2 | 10.4 | 9 |

It was observed that the compact powders 4 and 5 outside the invention not comprising non-volatile non-phenyl silicone oil in the binder phase had poor or mediocre pick up/pay off and lower impact strength than the compact powders 2 and 3 according to the invention.

EXAMPLES 6 AND 7 (INFLUENCE OF THE PRESENCE OF AN UNTREATED TALC)

The following compositions were prepared according to the same preparation method indicated for Example 1, except that the pulverulent phase comprises only phase P1 and does not comprise the nacre-based phase P2.

| Phase | Ingredients | Ex. 6 | Ex. 7* |
|---|---|---|---|
| P1 | Mica (Mearlmica SV) | 23.9 | 10 |
| | Untreated talc (Imperial 400 - Imerys) | — | 13.9 |
| | Boron nitride (Softouch Boron Nitride Powder CC6058 ® - Momentive Performance Materials) | 3 | 3 |
| | Mica (Sericite S-152-BC ® - Miyoshi Kasei) | 12 | 12 |
| | Nylon-12 (Orgasol 2002 EXD NAT COS ® - Arkema) | 4 | 4 |
| | Talc (and) methicone (surface-treated talc) (SI-2 Talc JA-46R ® - Daito Kasei Kogyo) | 5 | 5 |
| | Magnesium stearate | 2 | 2 |
| | Pigments: Titanium dioxide (Hombitan FF Pharma - Sachtleben) Iron oxide (Unipure Red LC 383 - Sensient) Iron oxides Sunpuro Red Iron Oxide C33-8001, Sunpuro Yellow Iron Oxide C33-9001, Sunpuro Black Iron Oxide C33-7001 - Sun) | 28 | 28 |
| L1 | Styrene/isoprene block copolymer (Kraton G1701 EU) | 0.72 | 0.72 |
| | Phenyl trimethicone (Dow Corning 556 Cosmetic Grade Fluid) | 3.6 | 3.6 |
| | C12-15 Alkyl benzoate (Finsolv TN ® - Innospec Active Chemicals) | 7.68 | 7.68 |
| L2 | Dimethicone 100 CST (Xiameter PMX-200 Silicone Fluid 100 CST) | 10 | 10 |
| | Sorbitan isostearate | 0.1 | 0.1 |
| | Caprylyl glycol | 0.5 | 0.5 |

*outside the invention

The pick up and pay off of the compact powders 6 and 7 with a foam applicator and with a brush and the impact strength were compared according to the same protocols indicated for Example 1.

The results of the comparative tests are given in the table below:

| Evaluations | Ex. 6 | Ex. 7* |
|---|---|---|
| Pick up/pay off with a foam applicator | 5 | 3 |
| Pick up/pay off with a brush | 4 | 2 |
| Impact strength | 13 | 8.8 |

It was observed that the compact powder 7 outside the invention comprising talc not surface-treated had less efficient pick up/pay off effects and poorer impact strength than the compact powder 6 according to the invention not comprising talc that is not surface-treated.

EXAMPLES 8 TO 10 (INFLUENCE OF THE HYDROPHOBIC FILM-FORMING POLYMER)

The following compositions were prepared according to the same preparation method indicated for Example 1, except that the pulverulent phase comprises only phase P1 and does not comprise the nacre-based phase P2.

| Phase | Ingredients | Ex. 8 | Ex. 9* | Ex. 10* |
|---|---|---|---|---|
| P1 | Synthetic fluorophlogopite (Synafil S115 ® - Eckart) | 13.9 | 13.9 | 13.9 |
| | Boron nitride (Softouch Boron Nitride Powder CC6058 ® - Momentive Performance Materials) | 3 | 3 | 3 |
| | Mica (Sericite S-152-BC ® - Miyoshi Kasei) | 12 | 12 | 12 |
| | Nylon-12 (Orgasol 2002 EXD NAT COS ® - Arkema) | 4 | 4 | 4 |
| | Talc (and) methicone (surface-treated talc) (SI-2 Talc JA-46R ® - Daito Kasei Kogyo) | 5 | 5 | 5 |
| | Magnesium stearate | 2 | 2 | 2 |
| | Pigments: Titanium dioxide (Hombitan FF Pharma - Sachtleben) Iron oxide (Unipure Red LC 383 - Sensient) Iron oxides Sunpuro Red Iron Oxide C33-8001, Sunpuro Yellow Iron Oxide C33-9001, Sunpuro Black Iron Oxide C33-7001 - Sun | 28 | 28 | 28 |
| L1 | Styrene/isoprene block copolymer (Kraton G1701 EU) | 0.72 | — | — |
| | Acrylates/polytrimethylsiloxymethacrylate copolymer (Dow Corning FA 4002 ID ® Silicone Acrylate) | — | 0.72 | — |
| | Trimethyl siloxysilicate (SR 1000 ®) | — | — | 0.72 |
| | Phenyl trimethicone (Dow Corning 556 Cosmetic Grade Fluid) | 3.6 | 3.6 | 3.6 |
| | C12-15 Alkyl benzoate (Finsolv TN ® - Innospec Active Chemicals) | 7.68 | 7.68 | 7.68 |
| L2 | Dimethicone 100 CST (Xiameter PMX-200 Silicone Fluid 100 CST) | 10 | 10 | 10 |
| | Sorbitan isostearate | 0.1 | 0.1 | 0.1 |
| | Caprylyl glycol | 0.5 | 0.5 | 0.5 |

*outside the invention

The compact powders 8 to 10 were compared as regards the impact strength according to the same protocol indicated for Example 1.

The results of the comparative tests are given in the table below:

| Evaluations | Ex. 8 | Ex. 9* | Ex. 10* |
|---|---|---|---|
| Impact strength | 13 | 11.2 | 7 |

It was observed that the compact powders 9 and 10 outside the invention comprising, respectively, a hydrophobic film-forming polymer of the acrylates/polytrimethylsiloxymethacrylate copolymer type and of the trimethyl siloxysilicate type had poor impact strength (<10), in contrast with the compact powder 8 according to the invention comprising an amorphous hydrocarbon-based block copolymer.

The invention claimed is:

1. A solid composition for coating keratin materials, in compact powder form, comprising a physiologically acceptable medium and at least:
    an oily phase in an amount of at least 20% by weight relative to the total weight of the composition; said oily phase comprising at least one non-volatile non-phenyl silicone oil which is a polydimethylsiloxane with a viscosity ranging from 50 to 500 cSt; and
    a pulverulent phase in an amount of at least 40% by weight relative to the total weight of the composition; said pulverulent phase comprising at least mica particles; and
    at least one amorphous hydrocarbon-based block copolymer;
    said composition not containing any talc particles that have not been surface-treated and being obtained via a process comprising:
        (i) the oily phase, the amorphous hydrocarbon-based block copolymer, the pulverulent phase and the volatile solvent(s) are mixed to form a slurry; and
        (ii) the slurry is formed in a container by compacting, in particular pressing and/or suction, to obtain the composition in powder form,
    wherein the at least one non-volatile non-phenyl silicone oil is/are present in a concentration ranging from 4% to 15% by weight relative to the total weight of the composition and wherein an impact strength of the solid composition measured by drops from a drop height of 30 cm required to split the solid composition is greater than or equal to 10.

2. The composition according to claim 1, in which the oily phase is present in a concentration of at least 20% by weight relative to the total weight of the composition.

3. The composition according to claim 1, in which said non-volatile silicone oil is chosen from oils with a viscosity at 25° C. ranging from 8 to 5000 cSt.

4. The composition according to claim 1, in which said non-volatile silicone oil is chosen from those corresponding to the following formula:

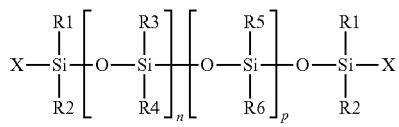

in which:
R1, R2, R5 and R6, which may be identical or different, denote an alkyl radical containing from 1 to 6 carbon atoms,
R3 and R4, which may be identical or different, denote an alkyl radical containing from 1 to 6 carbon atoms, a vinyl radical, an amine radical or a hydroxyalkyl radical containing from 1 to 6 carbon atoms,
X denotes an alkyl radical containing from 1 to 6 carbon atoms, an amine radical or a hydroxyalkyl radical containing from 1 to 6 carbon atoms,
n and p are integers such that the compound is liquid.

5. The composition according to claim 1, in which the content of pulverulent phase is greater than or equal to 40% by weight relative to the total weight of the composition.

6. The composition according to claim 1, in which the amount of oily phase and the amount of pulverulent phase are such that the oily phase/pulverulent phase weight ratio ranges from 20/80 to 45/55.

7. The composition according to claim 1, in which the mica particles are selected from the group consisting of sericites, muscovite micas and fluorophlogopite synthetic micas and mixtures thereof.

8. The composition according to claim 1, not containing any nacre and also containing mica particles with a mean size of at least 15 μm.

9. The composition according to claim 1, in which said pulverulent phase comprises at least one particulate colouring agent.

10. The composition according to claim 1, in which said amorphous hydrocarbon-based block copolymer comprises an amorphous copolymer formed by polymerization of an olefin.

11. The composition according to claim 1, in which said at least one amorphous hydrocarbon-based block copolymer comprises an amorphous block copolymer of styrene and of an olefin.

12. The composition according to claim 1, in which said at least one amorphous hydrocarbon-based block copolymer comprises an optionally hydrogenated copolymer, containing styrene blocks and ethylene/$C_3$-$C_4$ alkylene blocks.

13. The composition according to claim 1, in which said at least one amorphous hydrocarbon-based block copolymer comprises a styrene-ethylene/butylene-styrene triblock copolymer.

14. The composition according to claim 1, in which said at least one amorphous hydrocarbon-based block copolymer comprises a mixture of a styrene-butylene/ethylene-styrene triblock copolymer and of a styrene-ethylene/butylene diblock copolymer.

15. The composition according to claim 1, comprising a content inclusively between 0.5% and 5% by weight of hydrocarbon-based block copolymer(s) relative to the total weight of the composition.

16. The composition according to claim 1, wherein the composition is in the form of a foundation powder, a face powder or an eyeshadow.

17. A process for coating keratin materials, comprising: application to the keratin materials of a composition according to claim 1.

18. The composition according to claim 1, wherein the mica particles are present in a concentration ranging from 1% to 70% by weight relative to the total weight of the composition.

19. The composition according to claim 1, wherein the at least one hydrocarbon-based block copolymer(s) is/are present in a concentration ranging from 0.5% to 5% by weight of active material of hydrocarbon-based block copolymer(s) relative to the total weight of the composition.

20. A solid composition for coating keratin materials, in compact powder form, comprising a physiologically acceptable medium and at least:
    an oily phase in an amount of at least 20% by weight relative to the total weight of the composition; said oily phase comprising at least one non-volatile non-phenyl silicone oil which is a polydimethylsiloxane with a viscosity ranging from 50 to 500 cSt; and a pulverulent phase in an amount of at least 40% by weight relative to the total weight of the composition; said pulverulent phase comprising at least mica particles; and at least one amorphous hydrocarbon-based block copolymer;

said composition not containing any talc particles that have not been surface-treated and being obtained via a process comprising:
  (i) the oily phase, the amorphous hydrocarbon-based block copolymer, the pulverulent phase and the volatile solvent(s) are mixed to form a slurry; and
  (ii) the slurry is formed in a container by compacting, in particular pressing and/or suction, to obtain the composition in powder form, wherein the at least one non-volatile non-phenyl silicone oil is/are present in a concentration ranging from 4% to 15% by weight relative to the total weight of the composition, wherein the mica particles are present in a concentration ranging from 1% to 70% by weight relative to the total weight of the composition, wherein the at least one hydrocarbon-based block copolymer(s) is/are present in a concentration ranging from 0.5% to 5% by weight of active material of hydrocarbon-based block copolymer(s) relative to the total weight of the composition, and wherein an impact strength of the solid composition measured by drops from a drop height of 30 cm required to split the solid composition is greater than or equal to 10.

* * * * *